(12) United States Patent
Hepburn et al.

(10) Patent No.: US 6,942,629 B2
(45) Date of Patent: Sep. 13, 2005

(54) ADJUSTABLE SPLINT DEVICE FOR RELIEVING CONTRACTURES

(75) Inventors: George R. Hepburn, Severna Park, MD (US); Russell Vedeloff, Greensboro, MD (US)

(73) Assignee: Dynasplint Systems, Inc., Severna Park, MD (US)

( * ) Notice: Subject to any disclaimer, the term of this patent is extended or adjusted under 35 U.S.C. 154(b) by 162 days.

(21) Appl. No.: 10/677,540

(22) Filed: Oct. 2, 2003

(65) Prior Publication Data

US 2005/0075594 A1 Apr. 7, 2005

(51) Int. Cl.$^7$ .................................................. A61F 5/00
(52) U.S. Cl. ............................ 602/16; 602/23; 602/26
(58) Field of Search .............................. 602/5, 16, 23, 602/26, 32

(56) References Cited

U.S. PATENT DOCUMENTS

| | | | | |
|---|---|---|---|---|
| 649,237 A | * | 5/1900 | Dyson | 602/16 |
| 2,477,591 A | * | 8/1949 | Follis | 602/28 |
| 3,548,817 A | * | 12/1970 | Mittasch | 602/36 |
| 4,397,308 A | | 8/1983 | Hepburn | 128/88 |
| 4,485,808 A | | 12/1984 | Hepburn | 128/87 R |
| 4,489,718 A | * | 12/1984 | Martin | 602/16 |
| 4,508,111 A | | 4/1985 | Hepburn | 128/87 R |
| 4,608,971 A | * | 9/1986 | Borschneck | 602/23 |
| 5,014,690 A | * | 5/1991 | Hepburn et al. | 602/16 |
| 5,542,912 A | * | 8/1996 | Hess | 602/27 |
| 5,570,881 A | * | 11/1996 | Lau | 463/47.1 |
| 5,645,521 A | * | 7/1997 | Hepburn et al. | 601/33 |
| 6,001,075 A | * | 12/1999 | Clemens et al. | 602/16 |
| 6,245,034 B1 | * | 6/2001 | Bennett et al. | 602/20 |
| 6,361,513 B1 | * | 3/2002 | Rossi et al. | 602/16 |
| 6,413,231 B1 | * | 7/2002 | Berman et al. | 601/38 |
| 6,786,882 B2 | * | 9/2004 | Slishman | 602/36 |

* cited by examiner

Primary Examiner—Henry Bennett
Assistant Examiner—Amanda Wieker
(74) Attorney, Agent, or Firm—Armstrong, Kratz, Quintos, Hanson & Brooks, LLP; Hanson & Brooks, LLP

(57) ABSTRACT

In an adjustable splint assembly having a lower strut and an upper strut, and having there between a pivotably mounted head portion defining a cam surface, the improvement comprising the lower strut being provided with a loading screw, a spring and a spring spacer with a graduated number series thereon all contained within an inner housing tube with a single window and wherein the lower strut has an outer lower leg tube provided with a series of windows, and depending on the length of the lower strut, the graduated number series will register with a window in said series of windows and the window of the inner housing tube so that the amount of tension being applied by the loading screw can be read at that particular window of the outer lower leg tube.

8 Claims, 12 Drawing Sheets

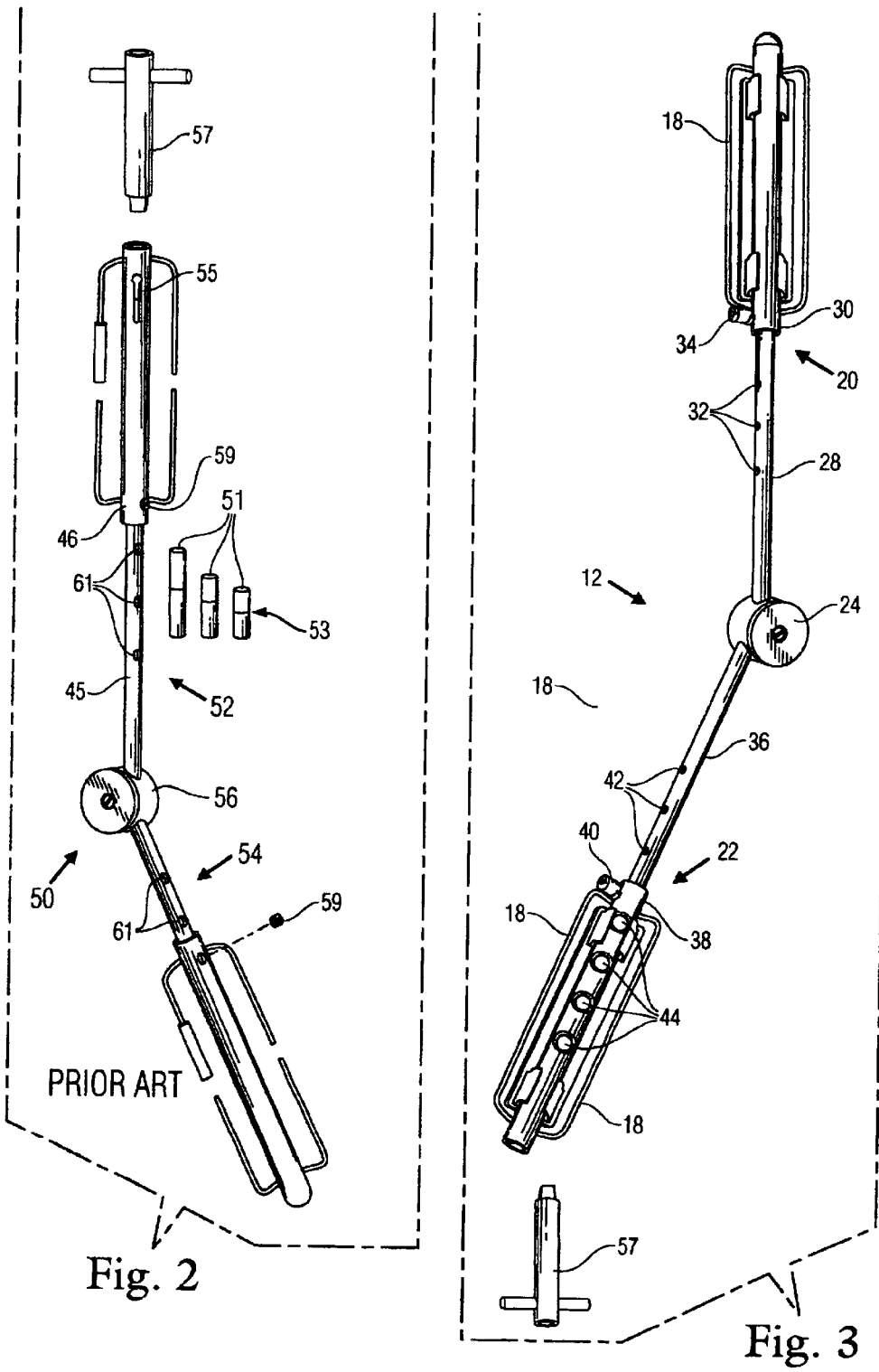

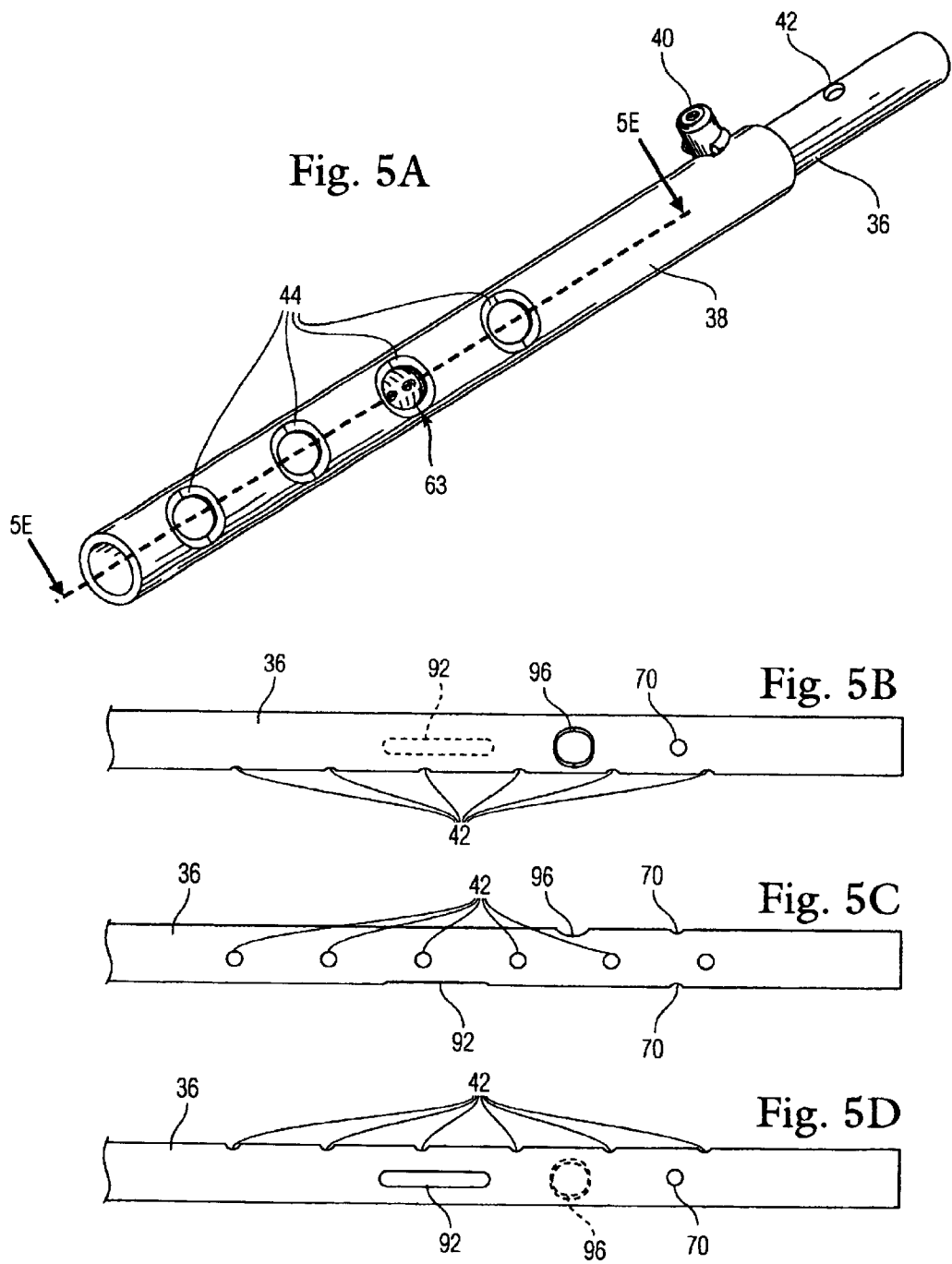

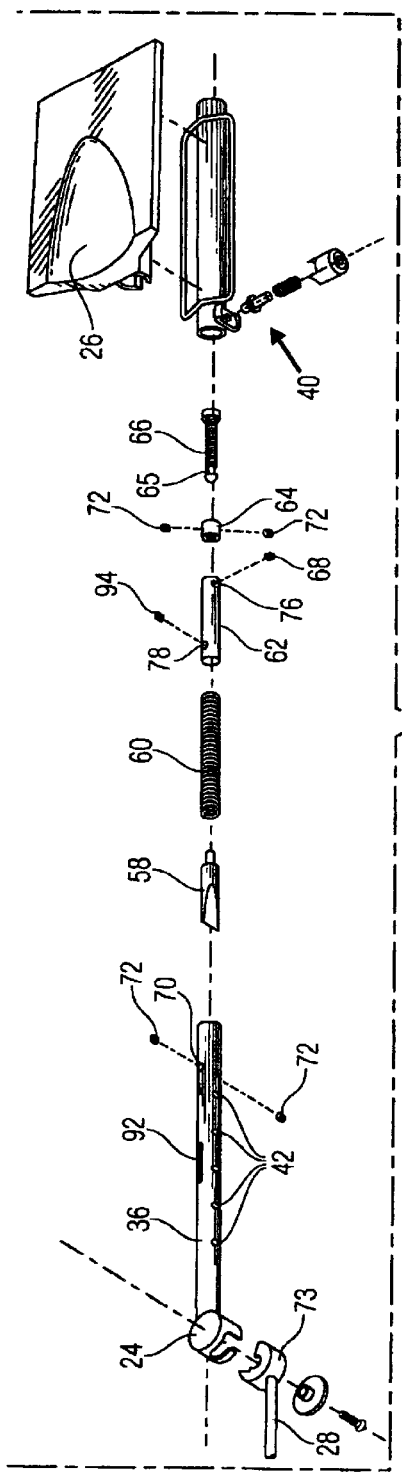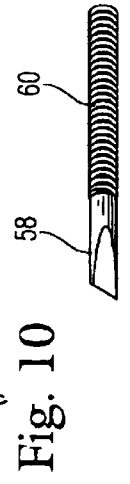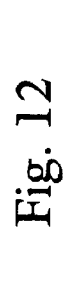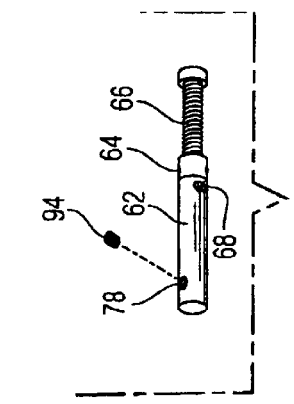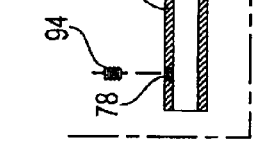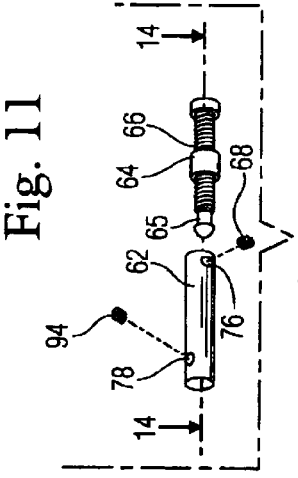

ADJUSTABLE SPLINT DEVICE FOR RELIEVING CONTRACTURES

FIELD OF THE INVENTION

The herein disclosed invention finds applicability in the medical field and is useful for bringing about mobility in a stiff-joint. More particularly, this invention relates to an adjustable splint useful in treating impairments in body joints such as knees, elbows, wrists and fingers.

BACKGROUND OF THE INVENTION

There are numerous instances where individuals develop contractures of a joint, as for example, the knee. Contractures of the knee may be brought about as a result of inactivity of the knee after surgery in the knee area, such as repair of a fracture or repair of a ligament. More specifically, the invention described herein is an improvement over analogous devices claimed in U.S. Pat. Nos. 4,397,308, 4,485,808 and 4,508,111 to Hepburn. The improvement will be more fully understood by a reading of the disclosure, in accompaniment with the attached drawings.

OBJECTS OF THE INVENTION

A major object of this invention is to produce an adjustable splint which is convenient to use.

Another object of this invention is to produce a splint with fewer detached parts.

A further object of the invention is to produce a splint allowing for easy graded adjustment of a quantifiable force to reduce contractures.

BRIEF SUMMARY OF THE INVENTION

The inventive concept is directed to an adjustable splint device for relieving contractures. The device can be applied to a joint, for example, the knee, elbow or finger in need of relief from contracture. While the inventive device can be used to treat a variety of body-joints, the herein disclosed invention has been drafted to be directed mainly to the knee. The inventive device is an improvement over existing-like adjustable splints for relieving contracture, in that the device can be accommodated various leg lengths without having to disassemble the device and changing parts. Besides the convenience of not having to change parts, there is also the added convenience of not having parts separated from the main device which will be lost.

Broadly considered, the invention is directed to an adjustable splint assembly having a lower strut and an upper strut, having there between a pivotably mounted head portion defining a cam surface, and the lower strut having at one end an adjustable biasing means biased into engagement with said cam surface, for applying a quantifiable force. The splint assembly has an improvement over the prior art in that the lower strut is provided with a loading screw, spring and a spring spacer contained within an inner housing tube which has a window and said inner housing tube being contained within an outer housing tube. The spring spacer has imprinted thereon a graduated number series. The inner housing tube has therein a window through which the graduated number series of the spring spacer would be visible and also on the inner housing tube, there are a series of holes into which a latch attached to the outer housing tube will lock to adjust the length of the strut. The latch arrangement can be replaced with the screw and hole arrangement or by other suitable means such as a cam clamp. The outer lower leg tube has a latch and a series of windows with each window of the series of windows being individually able to register with said graduated number series on the spring spacer and with the window of the inner housing tube such that with this arrangement the adjustable splint assembly is able to accommodate a variety of leg sizes without having to change the spring spacer. The adjustable splint assembly upper strut has an inner stem rod contained within an outer upper leg tube and wherein the inner stem rod has a series of holes longitudinally thereof and the outer upper leg tube is provided with a telescoping latch to engage inner stem rod holes and thus the length of the strut can be adjusted. The adjustable splint assembly telescoping pull latch firmly attached can engage with the holes of the lower inner housing tube. The adjustable splint is supplied with pads attached thereto to assure a comfortable fit of the splint on the patient and is also supplied with a binding means for attaching the adjustable splint device at the knee to the upper and lower part of the leg. An alternative adjustable splint device for relieving contracture can be formed using joined multiple adjustable splint assemblies.

BRIEF DESCRIPTION OF THE DRAWINGS

FIG. 2 is a perspective view of the prior art adjustable splint.

FIG. 3 is a perspective view of an adjustable splint of this invention.

FIGS. 5A–5F are views describing the lower strut lower leg tube and inner housing tube. FIG. 5A is a perspective view describing the lower leg tube, the lower inner housing tube and spring spacer graded scale; FIGS. 5B–5D are views of the lower inner housing tube; FIG. 5E is a cross-section thereof taken along lines 5E—5E of the lower leg tube and FIG. 5F is a front plan view thereof.

FIG. 6A is a perspective view of the spring spacer; FIG. 6B is a side plan view thereof; FIGS. 6C and 6D are schematic representations of the spring spacer.

FIG. 10 is an exploded view showing the components of the tension mechanism in the adjustable splint.

FIGS. 11–19 are views depicting how the tension mechanism is to be assembled.

DETAILED DESCRIPTION OF THE INVENTION

Figure 1:
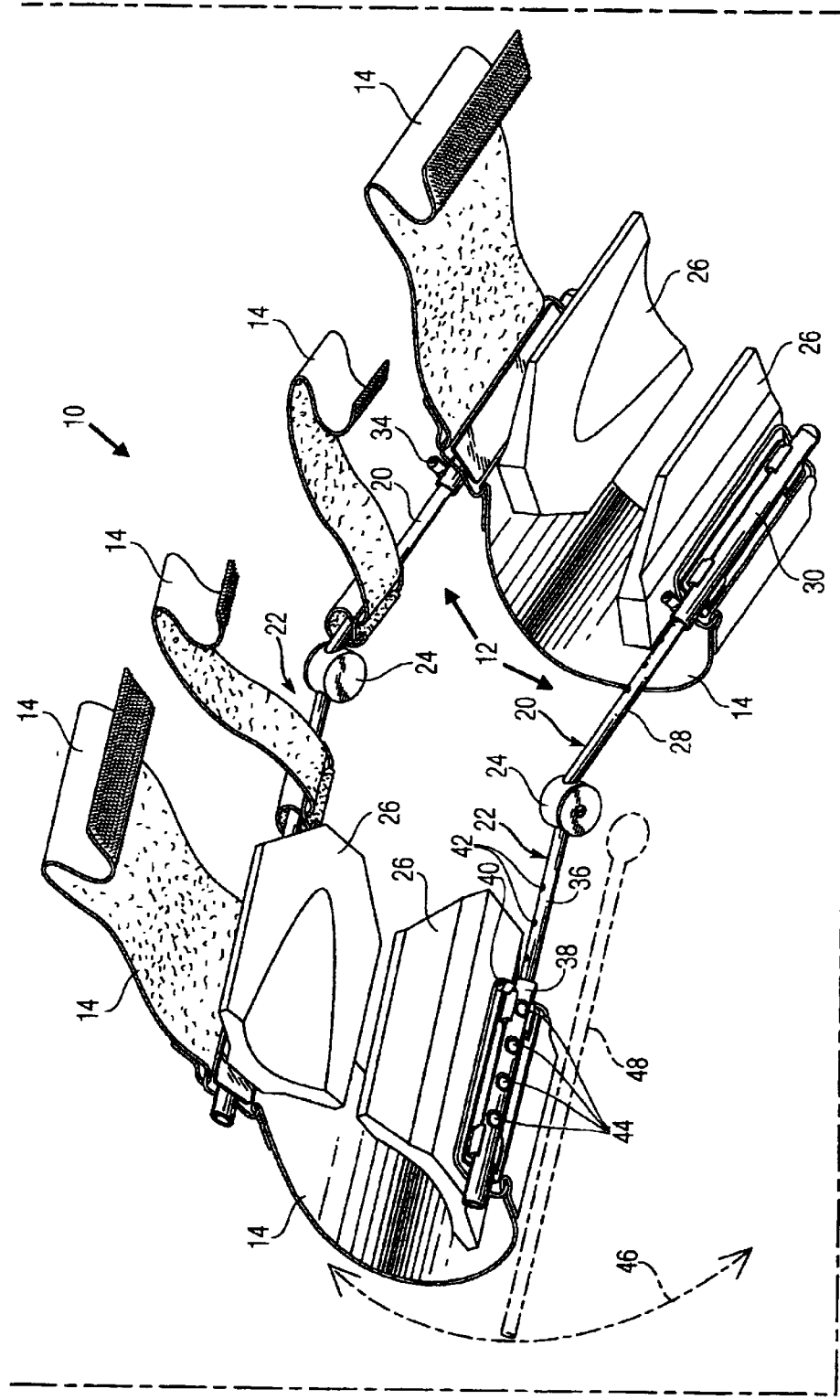
FIG. 1 is a perspective view of the Adjustable Splint Device for Relieving Contractures of the invention.

With reference to FIG. 1, the Adjustable Splint Device for Relieving Contracture 10 has a pair of adjustable splint assemblies 12 jointed together with velcro cuffs and counter force straps 14, although other securing means such as belts would be operative. Each adjustable or telescopic splint assembly 12 is comprised of an upper (or proximate) strut 20 and a lower (or distal) strut 22 which are joined through a head 24, shown in detail in FIG. 8. The upper or proximal strut 20 is comprised of an adjustable inner telescoping portion 28, an outer telescoping portion 30 along with positioning holes 32 (best shown in FIG. 3) and a telescopic latch lock 34 (best shown in FIG. 7) to be used for fixedly positioning the inner and outer telescoping portion (28, 30). The lower strut 22 (best shown in FIG. 3) is comprised of an adjustable inner telescoping portion or lower inner housing tube 36 and an outer telescoping portion or lower leg tube 38 along with a telescopic latch lock 40 and positioning holes 42 which are used with latch 40 to fixedly position the inner and outer telescoping portions of the lower strut (36, 38). The function of both the upper and lower telescoping struts is to properly adjust the struts to accommodate the length of the patient's thigh and leg. Note, particularly, that the outer telescopic portion 38 of the lower strut is provided with gauge windows 44 whose function will be more fully described with reference to FIGS. 5 and 6. As shown in FIG. 1, for purposes of comfort and providing a more effective fit, the telescoping struts 20, 22 are provided with cushioning pads 26. The dashed arrows 46 and the dashed lines 48 of the lower strut (FIG. 1) are intended to show pivotal motion between the upper and lower struts 20, 22.

With reference to FIGS. 2 and 3, there is shown a comparison between the prior art adjustable splint assembly 50 (FIG. 2); and the splint assembly 12 of the herein disclosed invention (FIG. 3). Referring to FIG. 2, the telescoping splint assembly 50 has a proximal strut 54 which abuts the thigh and a distal strut 52 which abuts the leg. The telescoping portions of the strut 52 are an inner member 45 and an outer housing member 46. These telescoping parts of the strut 52, 54 are positioned using a removable screw 59 inserted into a hole 61 to fixedly establish the length of the strut. Between these two struts, there is a head 56, the purpose of which will be explained as this disclosure is further read. Note that the distal telescoping strut 52, shown in FIG. 2, has supplied therewith a series of spring-spacer members 51 with a poundage indicator line 53 thereon. Also contained on the telescoping strut is a slot 55 having a calibration scale thereon (not shown). As explained below, as spring tension is applied, using the adjusting tool slotted driver 57, the degree of tension is registered between the poundage indicator line 53 and calibration scale on slot 55. The distal telescoping strut of the inventive splint assembly (FIG. 3) is significantly different from that of the prior art (FIG. 2). In the inventive device (FIG. 3) the outer telescopic portion or lower leg tube 38 of the lower strut 22 is provided with four windows 44 each individually to be in registry with the graduated scale 63 of spring spacer 62 (best shown in FIGS. 6A and 6B). This arrangement of windows and spring spacer is intended to properly accommodate the length of the telescoping strut 22 to the length of the leg of the patient being treated. Note particularly that the prior art telescoping strut was supplied with a series of spring abutting members or spacers of varying lengths 53 to fit between the spring and loading screw to accommodate different limb lengths to which the telescoping strut 52 was to be applied. The herein disclosed inventive device is designed to avoid the need for a series of spring spacer members 51 as required by the prior art device. The device of this invention requires only a single spring spacer member 62 (FIGS. 6A–6D). The value of the inventive device is that unlike as required by the prior art, the device does not have to be taken apart to insert a different spring spacer depending on the length of the strut vis-a-vis the length of the patient's leg. In addition as will be explained in greater detail below (FIG. 7), the inventive device has an attached latch 40 which replaces the detachable screws 59 of the prior art. The attached latch is convenient to use and avoids the possible loss of screws.

In FIG. 3, the adjustable splint assembly 12 of the invention has a proximal strut 20 to abut the thigh, a distal strut 22 to abut the leg and there between there is a head 24. The proximal end of the strut 20 has a telescoping portion composed of inner member 28 and an upper leg tube or outer member 30. The inner member 28 can also be referred to as a stem rod and the outer member 30 can be referred to as the upper leg tube. The distal strut 22 has a telescoping portion composed of an outer member 38 and an inner member 36. The outer member can be referred to as the lower leg tube and the inner member can be referred to as the lower housing tube. Note, also, that the upper strut 20 has on the inner member 28 holes 32 used along with telescopic latch 34 to adjust the length of strut 20. Likewise, the lower strut 22 has an inner member or lower inner housing tube 36 with holes 42 therein that along with telescopic latch 40 are used to fix the length of strut 22. An adjustment tool 57 is supplied to adjust the tension on the loading spring 60 (FIGS. 8 and 10–12) through the loading screw 66, as will be explained as the specification is read. Note that the loading screw 66 has a slot 67 (FIG. 8) for receiving adjustment tool 57. The function of windows 44 will also be explained as the specification is read.

Figure 4:
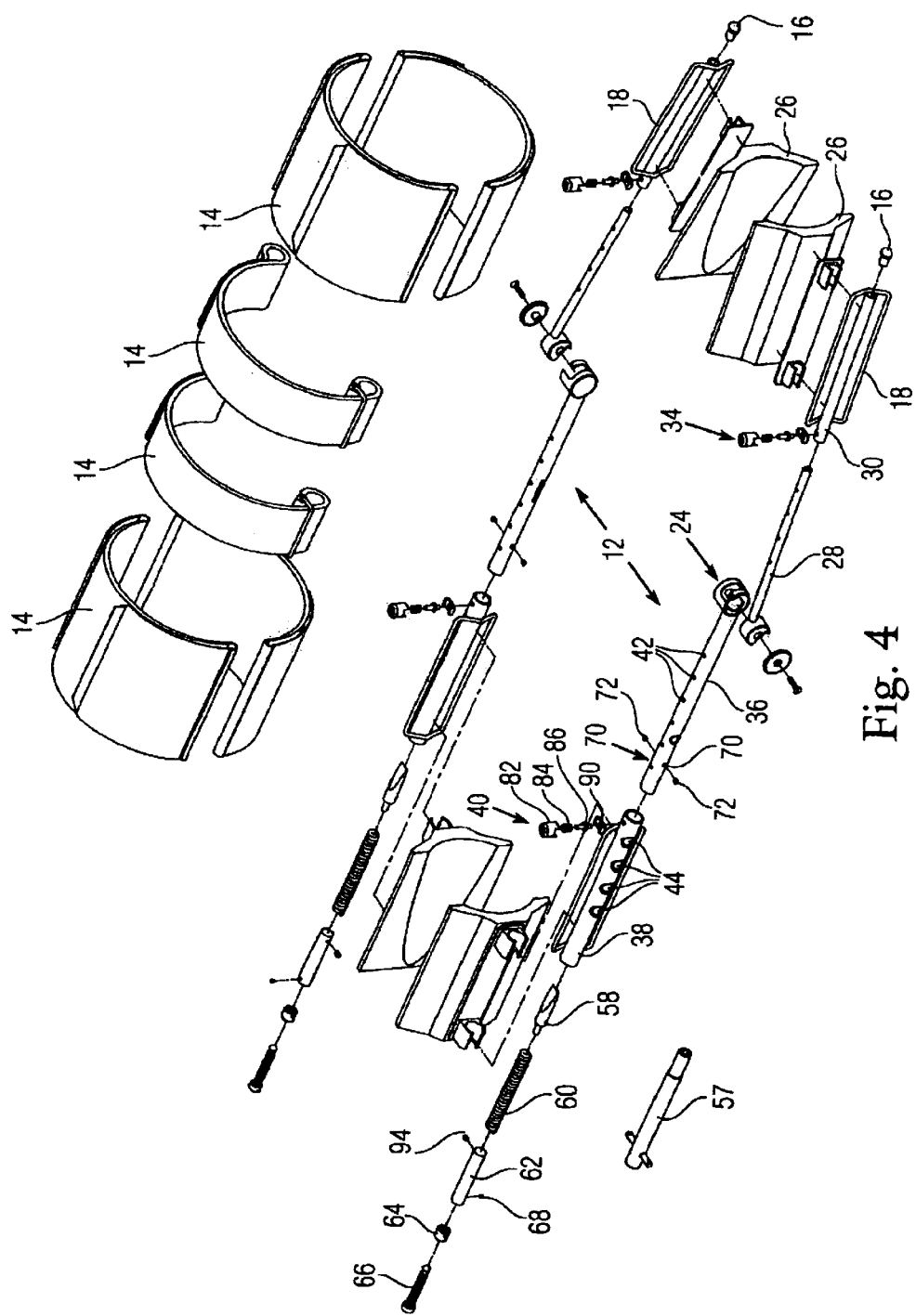
FIG. 4 is an exploded view of the adjustable splint device for relieving contracture of the invention.

With reference to FIG. 4, double adjustable splints 12 of the invention are illustrated as an exploded view showing the components which are used to create the device. Note that in FIG. 4, there are duplicate splints 12 which are substantially mirror images of one another. In use, equal tension is applied using the adjustment tool 57. As viewed from left to right, there is shown the loading screw 66, loading nut 64, spring spacer 62; spacer set screw 68, guide screw 94; spring 60, chisel tip 58, lower leg tube 38 with windows 44, inner housing tube 36 with holes 42, set screws 72, and holes 70, stem rod 28 outer lower leg tube 38 cap plugs 16. Also shown are the counter force straps and cuffs 14 winged pads 26, cuff wires 18 for retaining the counter force straps and cuffs 14 and cap plugs 16. The counter force straps and cuffs are made of velcro. The winged pads are intended to provide patient comfort.

With particular attention to FIGS. 3–6, the most important features of the invention are illustrated. These important features are to be found in the lower or distal strut 22. The distal strut 22 is a telescoping assembly which has an inner portion or housing tube 36 and an outer portion or lower leg tube 38. Inserted into the inner portion 36 in series are a chisel tip 58, compression spring 60, a spring spacer 62, a loading nut 64 and a loading screw 66 (best shown in FIGS. 4 and 10).

Figure 5E:
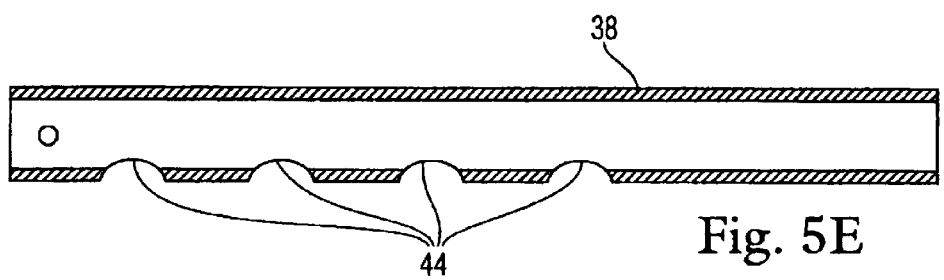
Figure 5F:
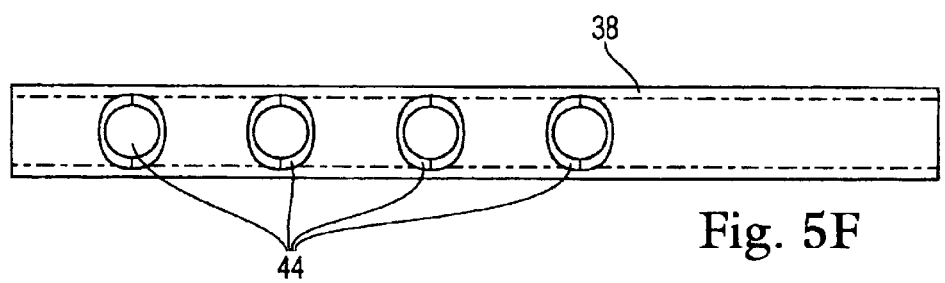

With particular reference to FIGS. 5A–5F views describing the multiple gauge windows of distal strut are described. FIG. 5A illustrates the lower leg tube 38 positioned over the lower strut inner housing tube 36 (broken away for ease of illustration). Four-gauge windows 44 are shown in the lower leg tube 38. Scale 63 is shown in greater detail in FIGS. 6A and 6B. The scale can be seen through one of the gauge windows 44. Note, also, that the lower leg tube 38 has telescopic latch 40 attached and positioned to be received into hole 42 to thereby secure the lower leg tube 38 to inner housing tube 36. FIGS. 5B–5D illustrate the structural features of the inner housing tube 36. FIG. 5B shows the inner housing tube with a single window 96 and screw hole 70 which would receive screw 72 (best shown in FIGS. 16–18). FIG. 5C turns the inner housing tube of 5B a quarter turn and shows holes 42 for receiving the telescopic latch 40. Holes 42 are employed to establish the length of the lower strut. FIG. 5D turns the inner housing tube 5C a quarter of a turn and shows the spring spacer guide slot opening 92. FIG. 5E is a cross-section of FIG. 5A showing windows 44 in the outer housing tube 38. FIG. 5F is a front plan view of the outer housing tube 38.

Figure 6A:
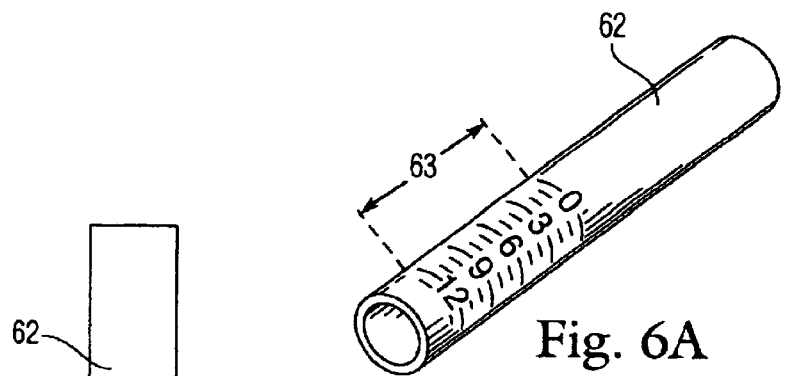
FIGS. 6A–6D are detailed views of the spring spacer.
Figure 6B:
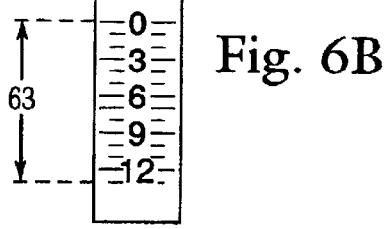
Figure 6C:
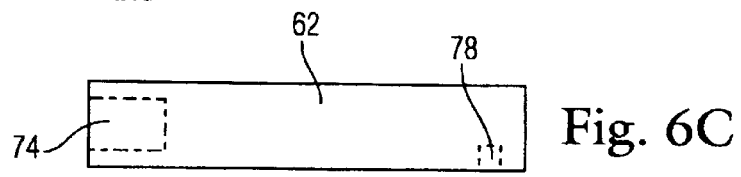
Figure 6D:
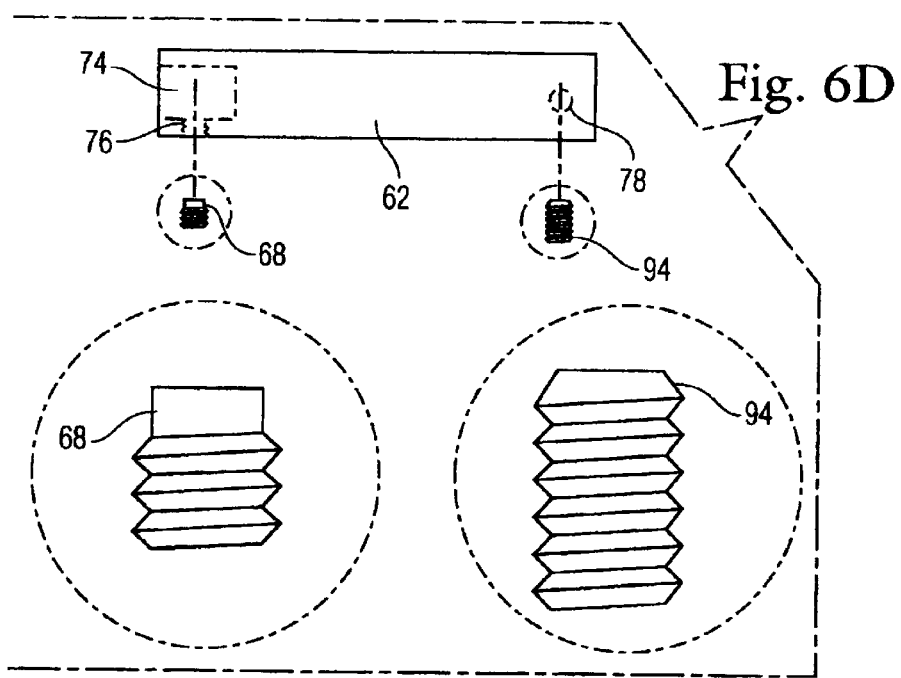
Figure 16:
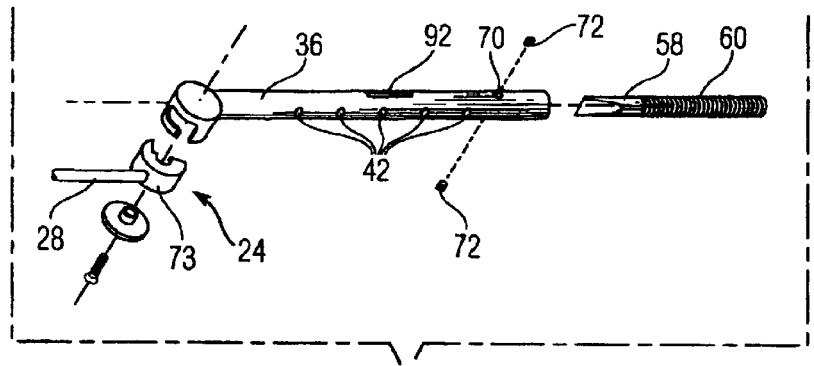
Figure 17:
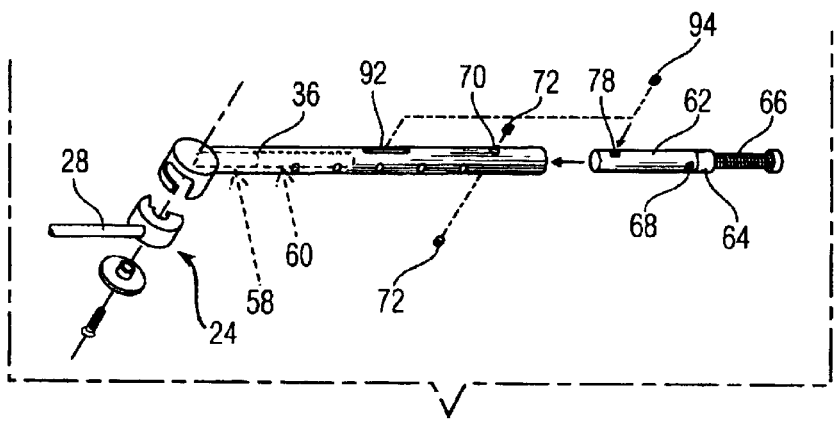
Figure 18:
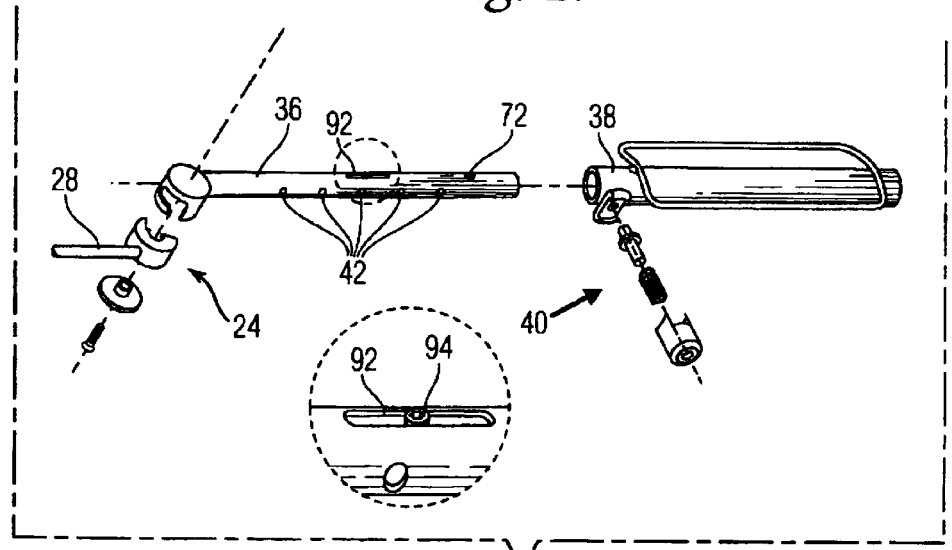
Figure 19:
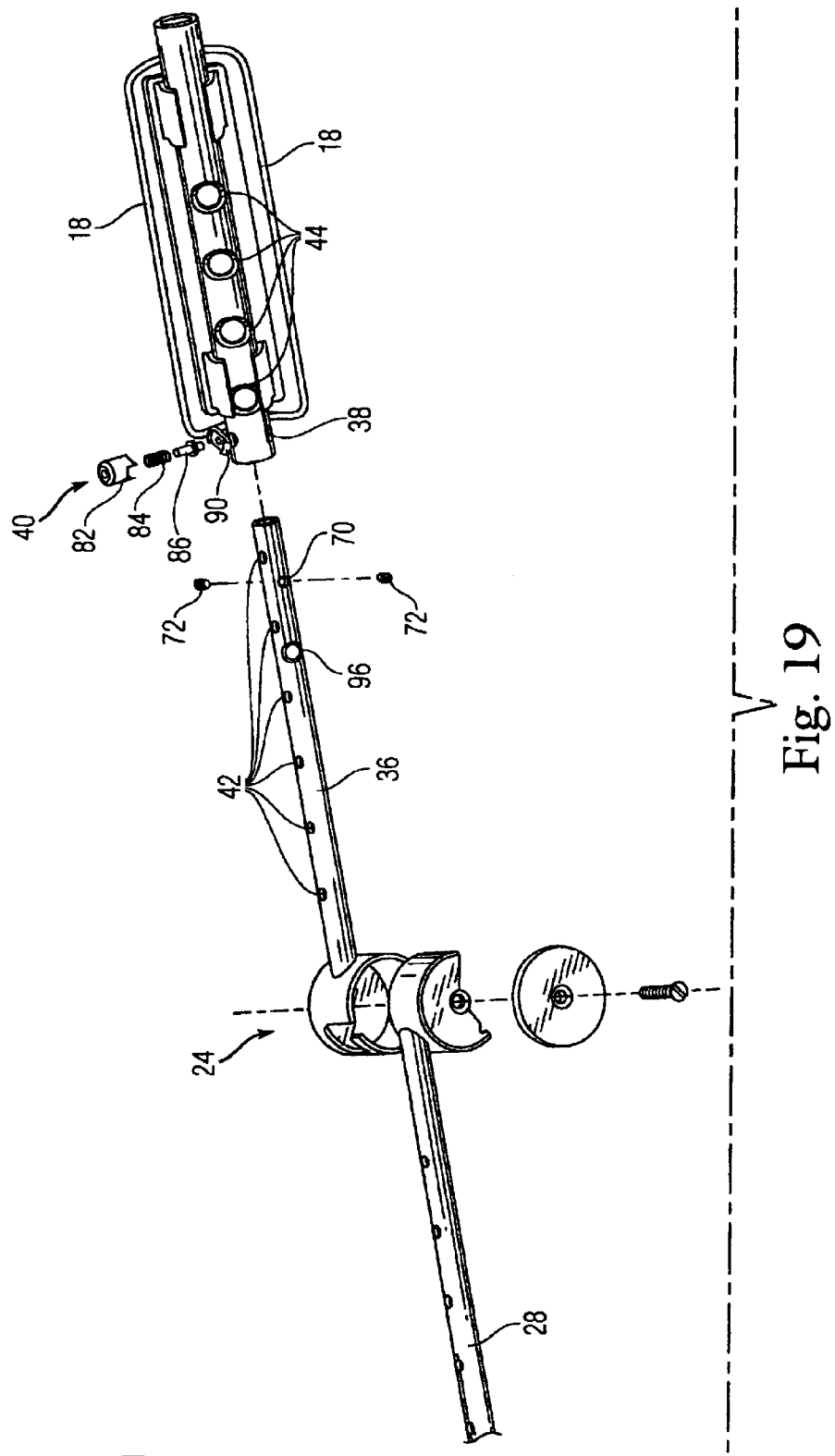

Referring to FIGS. 6A–6D, there is illustrated the spring spacer 62. In FIGS. 6A and 6B spring spacer 62 with the graduated scale 63 printed thereon is shown. With reference to FIGS. 6C and 6D, a schematic representation shows the opening 74 into which the loading screw 66 is inserted and the tapped hole 76 into which the loading screw and spring spacer set screw 68 (enlarged) is inserted to retain the loading screw 68 in the spring spacer 62, as best shown in FIGS. 6D, 13 and 14. Also shown in FIGS. 6C and 6D is tapped hole 78 which receives the guide screw 94 (enlarged) as best shown in FIGS. 16–18.

Figures 7A, 7B:
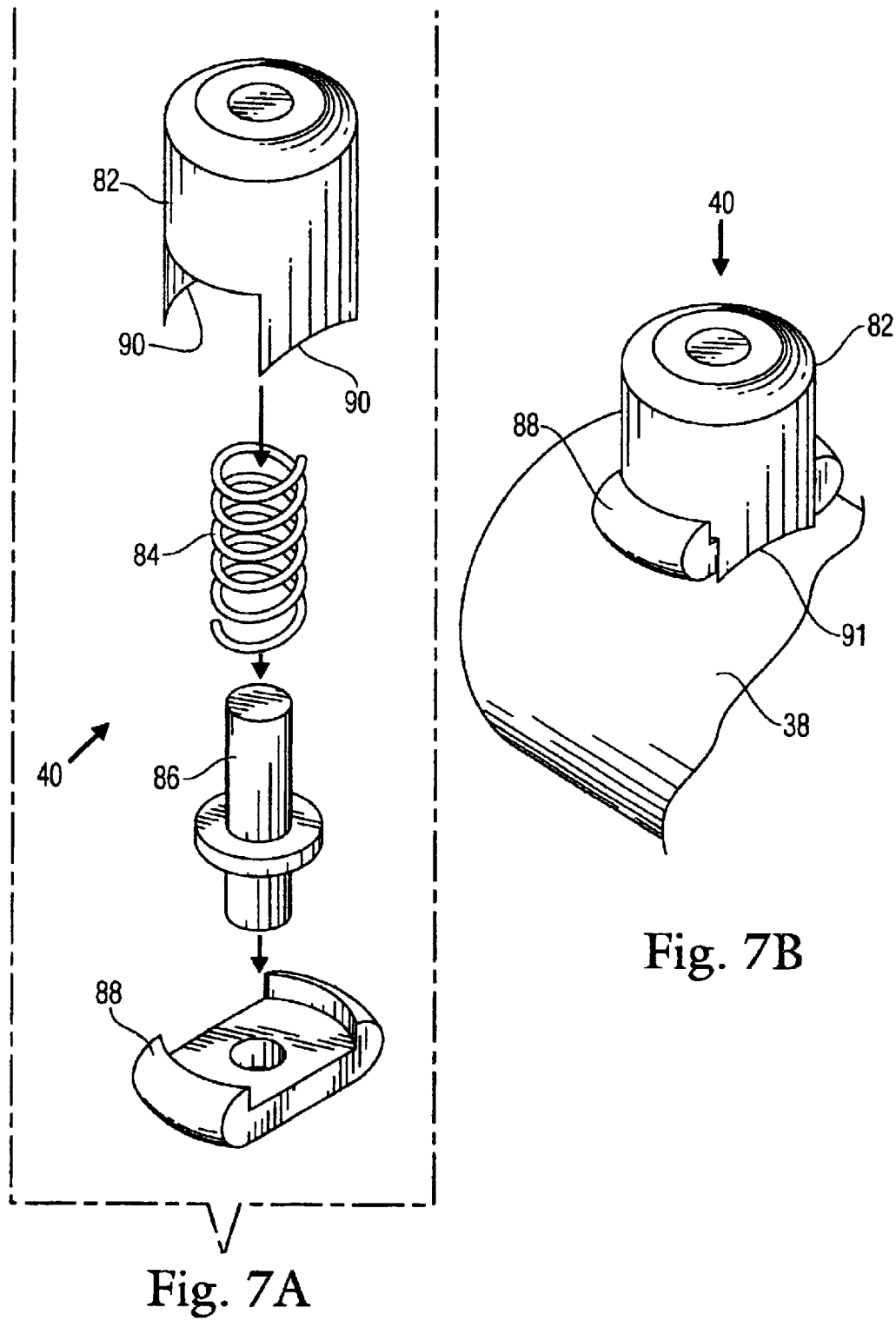
FIG. 7A is an exploded view of the parts forming the telescopic latch.
FIG. 7B is a perspective view of the telescopic latch attached to the lower leg tube.

Referring to FIGS. 7A and 7B, there is illustrated an exploded view (7A) of a telescopic latch 40 which is an elegant feature of this invention. In detail, FIG. 7A shows telescopic latch housing 82, a lock pin spring 84, the latch lock pin 86 and the latch plunger pull 88. Once the components are assembled (direction of the arrows) the bottom portion 90 of the telescopic latch housing 82 is welded 91 to the appropriate tube (7B). The upper and lower telescopic latch housings 40 and 34 are of slightly different geometries to fit the variance of tube radiuses of the upper tube 30 and lower leg tube 38. All other latch parts are identical.

While the telescopic latch is the preferred locking means of this invention, other lock and securing means as understood in the art could be used.

Figure 8:
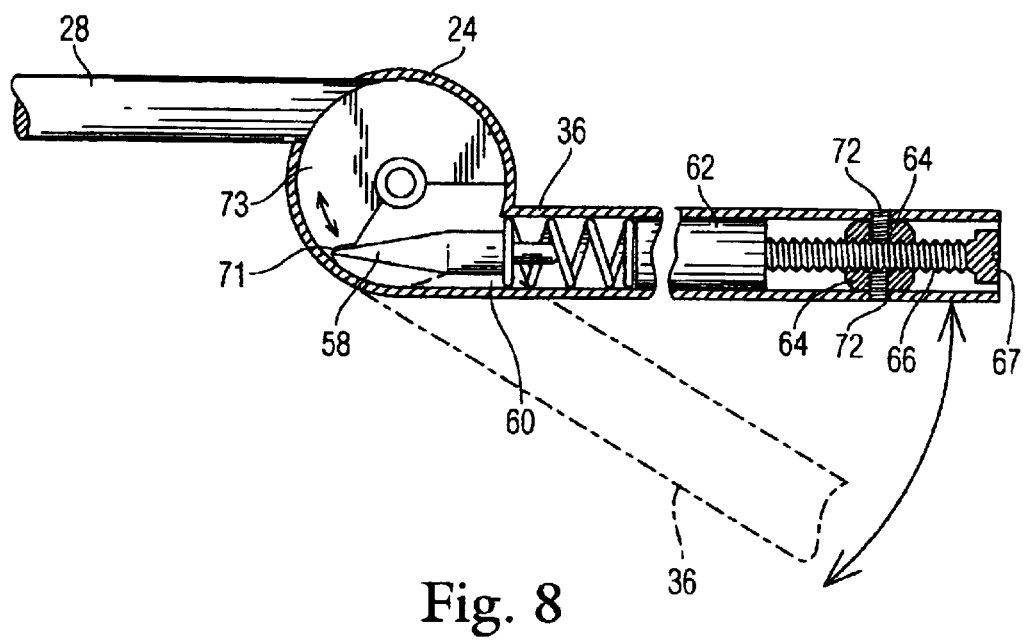
FIG. 8 is a detailed view of the head and tension mechanism used in this invention. Part of the housing tube has been broken away to show tension mechanism components.

FIG. 8 is a detailed view of the head 24 as used in this invention. Part of the housing tube 36 has broken away to show the tension mechanism. The main components of tension mechanism are the cam surface with indent, the chisel tip 58, spring 60, spring spacer 62, loading screw nut 64 and loading screw 66. The end of the loading screw is slotted 67 so as to receive an adjustment tool 57 to place or relieve tension on the spring. As has been previously pointed out, the head 24, as used in this invention, is the same as that used in the prior art. The arrow shows the direction of the inner housing tube 36 to produce tension on the leg.

The adjustable spring mechanism is comprised of a spring attached to a chisel tip that bears on a cam surface. In turn, a spring spacer abutting to a loading screw forces the chisel tip against the cam to produce a quantifiable force which will align the lower strut with the upper strut and produce tension on the joint to relieve contracture of the joint. As maximum deflection is reached, tension is created in the compression coiled spring. Tension on the spring is produced by the adjustment tool engaging and turning the loading screw. The turning of the loading screw creates greater compression on the spring, thereby exerting greater force on the cam surface to exert one way tension. The tension capability of the spring mechanism can range from 0 pounds to 12 pounds as shown on the graduations on spring spacer.

Figure 9:
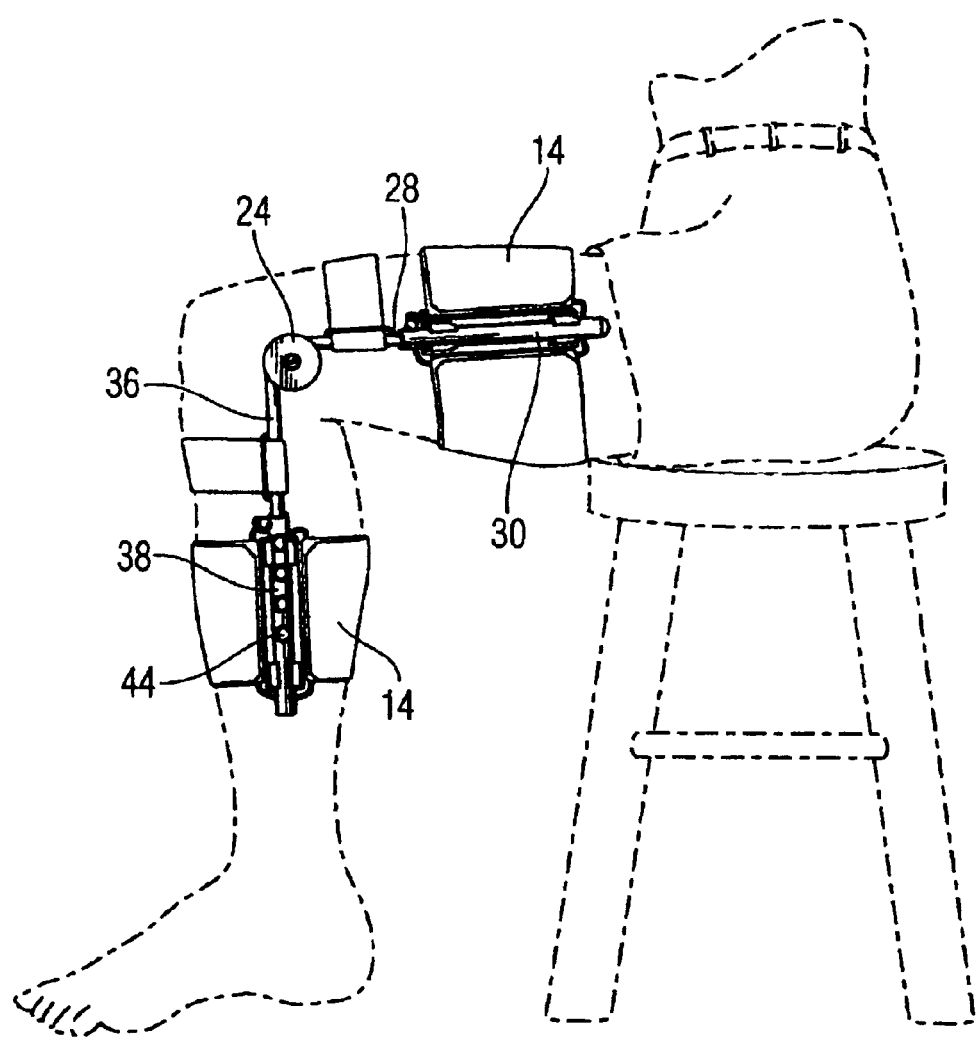
FIG. 9 is a view illustrating the application of the adjustable splint on a patient.

FIG. 9 is a pictorial view of the adjustable splint in use. The figure shows the adjustable splint device for relieving contracture applied to a patient. It is able to be applied to patients of different limb sizes without having to change any internal components. A simple adjustment of the length of the appropriate strut is all that is required. By this simple adjustment, the graduated scale will be in registry with the appropriate window.

With reference to FIGS. 10–19, the order for assembling the tension mechanism of the adjustable splint device is described. FIG. 10 is an exploded view showing the components of the tension mechanism. The order of assembly is as follows: First, insert stem rod and joint subassembly 28 into housing head 24. Then, insert the chisel tip 58 with the compression spring 60 mounted thereon into the housing tube 36 (FIGS. 11, 12 and 16). Establish that chisel tip 58 is correctly engaged with joint cavity 71 of joint 73 (FIG. 8). Next, with reference to FIGS. 13–15, join the spring spacer loading nut 64, loading screw 66 and spring spacer 62 by screwing the loading nut 64 onto the loading screw 66, until the loading screw groove 65 projects past loading nut 64 five threads; and then join the loading screw 66 with the spring spacer loading nut 64 attached thereto to the spring spacer 62 using the spring spacer set screw 68 (FIGS. 13 and 14). Referring to FIGS. 6C, 6D and 14, the loading screw 66 is inserted into the annular opening 74 of the spring spacer 62 and affixed with spring spacer set screw 68 applied through a tapped opening 76. With reference to FIGS. 15 and 17, next insert attached loading screw 66, spring spacer loading nut 64 into housing tube 36 and attach loading nut 64 to housing tube 36 through holes 70 using loading nut set screws 72. Next, align tapped spring spacer guide hole 78 with guide slot 92 in housing tube 36 and insert guide set screw 94 through slot 92 and into tapped guide hole 78 in spring spacer 62. Once this operation is completed (referring to FIGS. 18 and 19), the lower leg tube 38 can be inserted over the housing tube 36 and pads 26 positioned thereon. The lower leg tube 38 is to be joined to housing tube 36 using latch 40 attaching into holes 42. Note that FIG. 14 is a cross-section taken along 14—14 of FIG. 13; FIG. 18 shows slot 92 and guide set screw 94 enlarged and in FIG. 19 the splint of FIG. 18 is turned 180°.

It is also to be understood that the adjustable spring-loaded mechanism could be provided at either the lower or upper struts.

On theory while the lower strut is adjustable the upper strut could be of a fixed length.

The struts employed in the adjustable splint are preferably stainless steel, however, other materials of sufficient strength would be operative as would be understood by those skilled in the art. In addition, the struts employed herein are tubular, however, other configurations such as square or rectangular could be used.

The adjustable splint device of the invention can be applied to the knee as well as to other body joints and allowed to produce a graduated, quantified, adjustable tension with the ability to relax the stretch across the joint by extending the knee away from the limit of torsion. This will allow the tissue being stretched to have a rest period while not disturbing the adjustment of the spring tension and without having to remove the splint. In order to relieve the pressure of the contractured tissues, one merely has to overcome, by any means, the tension in the splint and extend the joint to a comfortable posture. Once a short rest is achieved, the splint may again exert its tension against the contractured tissue to help accomplish a greater degree of range of motion in the joint.

General instructions for applying and using the Adjustable Splint Device for Relieving Contracture are as follows:

1) Lay the leg into back-of-thigh and calf cuffs. The larger tubes with the window and scales should lie along the lower leg.

2) The cams should be equally aligned on either side of the knee and the tubes should line up with the centers of the side of the leg.

3) The velcro cuffs and counter force straps for the thigh and leg should be properly applied with the tightness such that one finger can slide between the cuff and the leg.

4) In use, the legs should not hang down. Lie on bed or support and elevate splinted leg.

5) Patients should wear the unit at the lowest tolerable tension setting for the longest time possible.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In an adjustable splint assembly having a lower strut and an upper strut, having there between a pivotably mounted head portion defining a cam surface, and the lower strut having at one end an adjustable biasing means biased into engagement with said cam surface, for applying a quantifiable force, the improvement comprising the lower strut being provided with a loading screw, spring and a spring spacer contained within an inner housing tube having a window and with said inner housing tube being contained within an outer lower leg tube, wherein the spring spacer has imprinted thereon a graduated number series;

the inner housing tube having therein a window through which the graduated number series of the spring spacer would be visible, and also on said outer lower leg tube, there is a securing means which will attach to the inner housing tube to adjust the length of the lower strut, the outer lower leg tube having a series of windows with each window of the series of windows being able individually depending on the length of the lower strut to register with said graduated number series on the spring spacer and with the window of the inner housing tube such that with this arrangement the adjustable splint assembly is able to accommodate a variety of leg sizes without having to change the spring spacer when the loading screw applies pressure to the spring and to the spring spacer which in turn applies pressure through the cam surface in the pivotably mounted head portion.

2. The adjustable splint assembly of claim 1 wherein the securing means comprises the outer lower leg tube having a telescopic pull latch firmly attached thereto so as to engage with the holes of the lower inner housing tube.

3. The adjustable splint of claim 1 wherein the securing means comprises a series of holes on the inner housing tube and a hole on the outer lower leg tube and a screw which can be used to join the inner housing tube and outer lower leg tube.

4. The adjustable splint assembly of claim 1 wherein the upper strut has an inner stem rod contained within an outer upper leg tube and wherein the securing means comprises the inner stem rod having a series of holes longitudinally thereof and the outer upper leg tube being provided with a latch to engage said inner stem rod in order to adjust length of the upper strut.

5. The adjustable splint assembly of claim 1 having pads attached thereto to assure a comfortable fit of splint on the patient.

6. An adjustable splint device for relieving contracture comprising the adjustable splint assembly claim 1 provided with a binding means for attaching the adjustable splint device at the knee to the upper and lower part of the leg.

7. An adjustable splint device for relieving contracture comprising multiple adjustable splint assemblies joined by a means to join said multiple adjustable splint assemblies and allow for efficient placement of the adjustable splint device on the leg and thigh and wherein each adjustable splint assembly which forms the adjustable splint device is an adjustable splint assembly as characterized by the adjustable splint assembly of claim 1.

8. In an adjustable splint assembly having a lower strut and an upper strut, having there between a pivotably mounted head portion defining a cam surface, and the lower strut having at one end an adjustable biasing means biased into engagement with said cam surface, for applying a quantifiable force, the upper strut having an inner stem rod and an outer upper leg tube and wherein the outer upper leg tube has a latch attached thereto to be received into holes in the inner stem tube, the improvement comprising the lower strut being provided with a loading screw, spring and a spring spacer contained within an inner housing tube having a window and with said inner housing tube being contained within an outer lower leg tube, wherein the spring spacer has imprinted thereon a graduated number series;

the inner housing tube having therein a window through which the graduated number series of the spring spacer would be visible, and also on said outer lower leg tube, there is a latch means which will attach to holes in the inner housing tube to adjust the length of the lower strut, the outer lower leg tube having a series of windows with each window of the series of windows being able individually depending on the length of the lower strut to register with said graduated number series on the spring spacer and with the window of the inner housing tube such that with this arrangement the adjustable splint assembly is able to accommodate a variety of leg sizes without having to change the spring spacer when the loading screw applies pressure to the spring and to the spring spacer which in turn applies pressure through the cam surface in the pivotably mounted head portion.

* * * * *

UNITED STATES PATENT AND TRADEMARK OFFICE
CERTIFICATE OF CORRECTION

PATENT NO.     : 6,942,629 B2
DATED          : September 13, 2005
INVENTOR(S)    : George R. Hepburn and Russell Vedeloff It is certified that error appears in the above-identified patent and that said Letters Patent is hereby corrected as shown below:

Column 8,
Line 28, "tube" should read -- rod --.

Signed and Sealed this

First Day of November, 2005

JON W. DUDAS
*Director of the United States Patent and Trademark Office*